United States Patent [19]

Morgan

[11] Patent Number: 4,708,965

[45] Date of Patent: Nov. 24, 1987

[54] METHOD OF TREATING HERPES VIRUS INFECTIONS WITH N,N'-DIACETYLCYSTINE AND DERIVATIVES

[76] Inventor: Lee R. Morgan, 725 Topaz St., New Orleans, La. 70124

[21] Appl. No.: 776,580

[22] Filed: Sep. 16, 1985

[51] Int. Cl.[4] ............................................ A61K 31/195
[52] U.S. Cl. .................................................... 514/563
[58] Field of Search ........................................ 514/563

[56] References Cited

PUBLICATIONS

Chemical Abstracts, 67:89342s (1967).

*Primary Examiner*—Jerome D. Goldberg
*Attorney, Agent, or Firm*—Klarquist, Sparkman, Campbell, Leigh & Whinston

[57] ABSTRACT

A method of treating herpes, comprising the step of applying to the herpes lesions a compound that interferes with leukotriene production, the compound being selected from the group consisting of N,N'-diacetylcystine, N-acetylhomocysteine and N-acetylcysteine.

6 Claims, No Drawings

METHOD OF TREATING HERPES VIRUS INFECTIONS WITH N,N'-DIACETYLCYSTINE AND DERIVATIVES

BACKGROUND OF THE INVENTION

1. Field of the Invention

This invention relates to treatment of herpes virus infections. More specifically, it concerns treatment of such infections with N,N'- diacetylcystine, N-acetyl homocysteine and N-acetylcysteine by interfering with leukotriene production.

2. General Background of the Invention

The large family of viruses known as the herpes viruses attack the skin and mucous membranes to produce both local eruptions and ulcers as well as generalized systemic symptoms of infection such as headaches, fever and malaise. The most common herpes viral infections are with herpes homonis simplex I and II.

There are generally two types of herpes infection viruses. Those produced by the herpes simplex are characterized by the eruptions of one or more groups of vesicles or sores on the human body, especially on the vermillion border of the lips, at the external nares, on the glans, prepuce or vulva.

Herpes simplex virus type 1 is known as the "skin" or "above the umbilicus" virus and type 2 is known as the "genital"or "below the umbilicus" virus. The types cannot be distinguished in a culture, but can be distinguished on the basis of the antibodies generated upon exposure to the virus. The two types cross react with one another in the laboratory and are, thus, very closely related to each other.

Herpes infections have been called, according to their sites, fever blisters, cold sores, herpes catarrhalis, herpes facialis, herpes febrilis, herpes genitalis, herpes labialis, herpes preputialis, herpes mentalis, herpes progenitalis, intrauteine herpes, etc. The infection is commonly recrudescent and reappears during other febrile illness or even physiological states such as menstruation and high stress.

Those lesions produced by herpes zoster develop along nerve sheaths with eruptive lesions in a linear patterns along dermal distributions of nerves on the face, trunk, abdomen, and extremeties producing extremely painful, eruptive, weeping lesions that heal extremely slowly with paraphesia. This type of infection is known as shingles and is seen in patients with cancer and opportunistic debilitating infections that depress the immune system of the patient.

Various treatments for herpes hominis simplex have been proposed. Asculai, U.S. Pat. No. 4,147,803, reports that certain sorbitan derivatives have antiherpetic activity. DeLong et al., (U.S. Pat. No. 3,639,612) described such activity for certain chalcogen containing heterocyclic compounds. Stedman, (U.S. Pat. No. 3,555,355), discloses that certain cycloalkylamines have activity against herpes simplex as does cycloheximide, (U.S. Pat. No. 4,427,684). Fleming et al., (U.S. Pat. No. 3,829,578), teaches that certain bis-basic ethers and xanthen-9-ones have anti-viral activity and Soichet, (U.S. Pat. No. 4,312,884), describes such antiviral activity by Spectinomycin.

Kaufman et al., (Arch. Ophthalmol. 68: 235-239 (1962)), reported treatment of herpes simplex keratitis with 5-iodo-2-deoxyridine (IUD). Schabel describes treatment of genital herpetic infection with 9-beta-D-arabino-fluranosyl adenine (Chemotherapy 13: 321-338 (1968)), and reported antiviral activity of 5-trifluoromethyl-2-deoxyuridine, (N.Y. Acad., Sci. 130: 168-180 (1965)). Adams et al., (J. Infect. Dis. 133 (suppl) 151-159 (1976)), treated genital herpes infections with topical application of adenine arabinside. Felber et al., (JAMA 223: 289-292 (1973)), described treatment of herpes infections by application of a vital dye as neutral red or proflavine followed by exposure to light. Chese-man et al., (N. Eng. J. Med. 300: 1345-1349 (1979)), and Pazin et al., (N. Engl. J. Med. 301: 225-230 (1979)), report the treatment of herpes simplex infection by human leukocyte interferon. Blough and Giuntoli, (JAMA 241: 2798-2801 (1979)), described treatment of human genital herpes infections with 2-deoxy-D-glucose. Schaeffer et al., (Nature 272: 583-585 (1978)), Fyfe et al., (J. Biol. Chem. 253: 8721-8727 (1978)), Sely et al., (Lancet 2: 1257-1270 (1979)), Park et al., (J. Infect. dis. 140: 802-806 (1979)), and Pavan-Langston et al., (Am J. Ophthalmol. 86: 618-623 (1978)), reported treatment of herpes infections by 9-(2-hydroxyethoxymethyl)guanine (Acyclovir). Fisher (Cutis 29: 467-472 (1982)), described treatment of herpes simplex infections with Amantadine Hydrochloride. Other forms of treatment of herpes hominis simplex Type I and II include a variety of agents such as lysine, ascorbic acid, topical ether and topical chloroform, thymol, nonionic surfactants, (U.S. Pat. Nos. 4,147,803, and 4,185,097) inactivated herpes viruses, zinc, urea, tannic acid, (U.S. Pat. No. 4,285,934), glutaraldehyde, cow pox vaccine, intradermal injections of gamma globulins, and a surgical treatment by epidermal excisions of the herpetic lesions.

Recently a mixture of L-lysine, gibberellic acid and urea has been reported to be useful in the treatment of H. simplex (U.S. Pat. 4,424,232). Similarly, transfer factor has been reported to be useful in the treatment of herpes simplex (U.S. Pat. No. 4,435,384). Adenosine monophosphate has recently been reported to reduce pain and increase healing of herpes zoster lesions (JAMA).

None of these prior art methods have proved satisfactory in treating skin ulcers caused by herpes virus-infections. If is accordingly the principal object of the present invention to provide a new method of treating herpes simplex by topical administration of a medication having good activities against herpes simplex and zoster and which further acts very quickly to effect essentially total relief of pain from the affected area.

These and other objects and advantages of the invention will become apparent from the following description.

SUMMARY OF THE INVENTION

The treatment of the herpes infection in accordance with this invention comprises topical application of the composition disclosed herein to the affected area on the person suffering from the infection. An effective amount of the composition is applied to the affected area 4 to 6 times a day until healing is effected. Generally, complete healing, i.e., disappearance of symptoms including lesions, will be achieved within about 4 to 14 days. The total relief of pain from the affected area will be achieved within several hours, generally from about 4 to 24 depending upon the median size of the lesions when treatment is started.

The composition in accordance with the present invention is effective in the treatment of areas on the human body affected with herpes simplex virus. The composition has been shown to bring very quick relief from the pain experienced by such conditions. The present composition also acts as an aid in healing of the condition and is effective in combating herpes simplex, zoster and related herpes infections.

The useful compounds of the present invention are N,N'-diacetylcystine, N-acetylhomocysteine or N-acetylcysteine. N,N'-diacetylcystine (N-DAC) has the formula

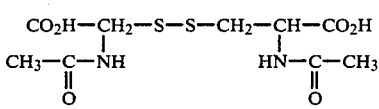

while N-acetyl homocysteine (NAH) has the formula

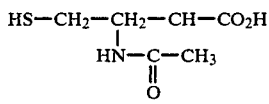

and N-acetyl cysteine (NAC) has the formula

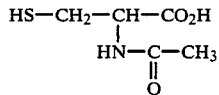

All three of these compounds are derivatives of the amino acids cysteine and cystine. The present inventor has discovered that these agents can very effectively reduce pain and increase healing of skin vesicles, ulcers and eruptions from Herpes Zoster and Herpes Simplex which have been found to be caused by leukotriene production.

The agents are preferably contained in a pharmaceutically inert carrier comprised of water. A preservative such as EDTA, 0.1%, may be included. The composition of this invention contains, on a weight basis, 20% N-DAC, NAC or NAH, and 0.1% EDTA, with the balance being a pharmaceutically inert carrier comprised of water.

STARTING MATERIALS

NAC is commercially available from Aldrich Chemical Company, Milwaukee, Wisc. in the United States and Europe. It is the acetyl amide of the amino acid cysteine. Its use has predominantly been as a mucolytic agent in the treatment of bronchial congestion and bronchitis. It chemically disrupts disulfide bonds in intra brondinal mucin, thus liquifying bronclinal mucous plugs.

NAH can be purchased from Fluka Chemical Company of Switzerland.

N-DAC can be synthesized in the following manner:

1-Cystine (0.05 mole, 12 g) was suspended in 50 ml of water and dissolved by adding 8 M potassium hydroxide until the solution was pH 12. At 0° C. to 3° C., acetic anhydride (0.15 mole 15.3 g) was added in small portions as the pH of the solution was maintained between 10 and 10.5 with 8 M potassium hydroxide. After the addition of acetic anhydride, the solution was allowed to stand one hour at room temperature at pH 10 and then adjusted to pH 3 with concentrated hydrochloric acid. The solution was concentrated in vacuo, and the viscous residue extracted three times with 100 ml portions of an acetone-water mixture (93:7 v/v). The acetone extract was concentrated in vacuo and dried in a desiccator over phosphorus pentoxide and sodium hydroxide. The residue was dissolved in ethanol. The precipitate that formed was removed by centrifugation and the remaining solution chromatographed on Silica Gel-G (Woelin). The columns were developed with chloroform: methanol: acetic acid (80:15:10v/v). The columns were cut at $R_f=0.4$ and the N-DAC eluted with methanol. The methanol eluent was concentrated in vacuo to dryness over phosphorus pentoxide. The residue was dissolved in ethanol and the disulfide precipitated by adding the ethanolic solution to diethyl ether. Yield 22%, m.p. 273-275, anal. calc. for $C_{10}H_{16}N_2S_2O_6$: C, 35.46; H, 5-20; N, 8-27%. Found: C, 35-94; H; 5.24; N, 8.17%.

MECHANISM OF ACTION

The present inventor has determined that the inflammation associated with herpes infections is a result of significant quantities of the leukotriene inflammatory mediators at the site of the herpic vesicles. The inflammatory process that accompanies the infections results from tissue membrane destruction with the release of arachidonic acid which results in leukotrienes that are mediators of ischemia, arterial constriction and epithelia destruction.

Leukotrienes (LTs) are members of the eicosanoid family, and are the major biologically active eicosanoids of the lipoxygenase pathway of arachidonic acid metabolism. This pathway is illustrated schematically below:

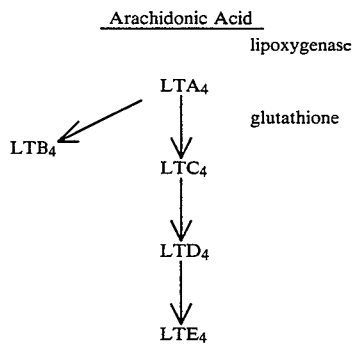

$LTA_4$ is the precursor of $LTB_4$ a potent chemotactic agent, and the LTs (i.e., $LTC_4$, $LTD_4$, and $LTE_4$), are associated with the slow-reacting substances of anaphylaxis.

LTs are produced by a host of cell types including the pulmonary parenchymal cells, macrophage, mast cells, leukocytes, connective tissue cells, and several types of smooth muscle cells, particularly vascular smooth muscle cells. When tissue and cellular membranes are destroyed by chemical, or some other foreign irritation, arachidonic acid is released which initiates the above cascade to the leukotrienes and other chemical mediators of inflammation.

LTs exert a variety of biological actions that could contribute to their role as mediators of ischemia and shock. In this connection, $LTB_4$ plays a key role as a mediator of inflammation by virtue of its chemotactic and chemokinetic properties on blood cells (e.g., eosinophils, macrophages). $LTB_4$ also promotes the release of lysosmal hydrolases from these and other cell types accompanied by an enhancement of microvascular permeability.

In contrast to LTB$_4$, the LTs (e.g., LTC$_4$, LTD$_4$, LTE$_4$,) are more active as stimulators of smooth muscle contraction. LTC$_4$ is metabolized to LTD$_4$ and then to LTE$_4$ and there is a significant loss of biological activity as metabolism progresses. Although LTC$_4$ and LTD$_4$ are comparable to each other in activity, they are both much more active than LTE$_4$ in most biological systems.

LTB$_4$, LTC$_4$ and LTD$_4$ are mediators of inflammation. As long as these agents are produced, because of continuous exposure to chemicals, virus-induced epithelial destruction, etc., the above LTs as well as other inflammatory factors will be produced. Of significant importance is that LTC$_4$ and LTD$_4$ are one in the same as the long acting substances of inflammation that also produce anaphylactic reactions to toxicity and drugs. The present inventor has established that there are elevated concentrations of tissue leukotrienes A$_4$ (LTA$_4$), C$_4$ (LTC$_4$) and D$_4$ (LTD$_4$) associated with herpes vesicles.

In general, the inventor has established that tissue damage is initiated by virus induced leukotriene release and propagated by the continued presence of inflammatory mediators. When N,N'- diacetylcystine (N-DAC), N-acetylcysteine (NAC) or N-acetylhomocysteine (NAH) is applied topically to open ulcers, inflammation is reduced and healing is promoted without the need for surgical debridement or other treatments. N-DAC, NAC and NAH exhibit their use as agents to reverse herpes induced skin necrosis and interact with peroxides and leukotriene A$_4$ (LTA$_4$) to reduce toxic free radicals and interrupt the leukotriene escade to the highly inflammatory slow releasing substances of anaphylaxis (SRS)-LTC$_4$ and LTD$_4$.

In the claimed embodiments, N-DAC, NAH or NAC can be used. Preferably N-DAC or NAH can be used, while most preferably N-DAC is used.

TOPICAL ABSORPTION IN MAN AND ANIMALS

There are no detectable blood levels of NAC, NAH or N-DAC following the application of 20% concentrations of these agents in water three times a day to patients with open ulcers. In the rabbit animal model that was described previously (Cancer Treat. Rep. 65: 1001, 1981) neither NAC, N-DAC or NAH could be detected in the animals circulation after topical application of 20% solution of the above agents to the surfaces of rabbit ears.

The present inventor has found that N-DAC and NAC interact with LTA$_4$ to produce a NAC adduct, thus by-passing the formation of the tissue irritats LTB$_4$, LTC$_4$ and LTD$_4$. The identified LTA$_4$-NAC adduct is described below and has no inflammatory properties when injected into rabbit skin. The adduct which is obtained is shown below.

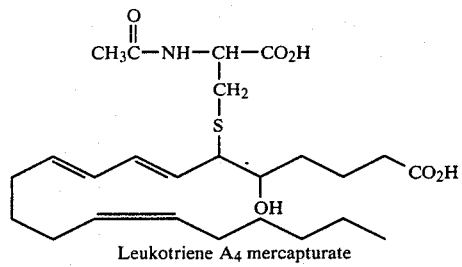

Leukotriene A$_4$ mercapturate

METHOD OF USE

In accordance with the present invention, twelve patients with cutaneous ulcers resulting from herpes infections were studied. Wet gauze compresses of 20% N-DAC were applied to four of the patients four times a day. In all cases, there was reduction in pain and inflammation within 48-72 hours. All lesions were cultured for baterial contamination, and when needed topical garamycin cream (0.1%) was applied twice daily along with the NAC solutions. All four patients demonstrated complete healing which did not require additional therapy. Debridement of scar formation was performed as needed to allow the deep penetration of N-DAC. Complete healing with minimal scarring was the result of the above application of N-DAC.

Six additional patients with ulcers received topical applications of 20% NAC in water as soaked gauze pads applied to the lesions four to six times a day. All patients treated with NAC exhibited healing and did not require any additional treatment.

Two additional patients were treated with 20% NAH in similar manners with 100% healing.

Two of the cases treated are described in detail below:

Case 1: A 78 year old male presented with herpes zoster over his left chest wall for seven days duration. The lesions were becoming worse with more drainage and pain. There were clusters of open ulcers with new vesicles developing each day. He was treated four times a day for thirty (30) minutes each time with wet gauze pads soaked with 20% N-DAC. The lesions became painless in 24 hours and all healed in two weeks. No recurrences were noted.

Case 2: A 56 year old male developed a herpes genital ulcer on his penis. It was an isolated lesion, extremely painful and draining. He was treated topically with moist gauze pads of 20% N-DAC four times a day and the lesion was painless in 24 hours and healed in 10 days. No recurrence was noted in six months.

I claim:
1. A method of treating herpes lesions in humans, comprising the step of:
applying to the herpes lesions a therapeutically effective amount of a compound sufficient to reduce inflammation of the lesions, the compound being selected from the group consisting of N,N'-diacetylcystine, N-acetylhomocysteine and N-acetylcysteine.
2. The method of claim 1 wherein the compound is topically applied to the lesions.
3. The method of claim 2 wherein the compound is applied to the lesions as a 20% solution.
4. The method of claim 1 wherein the compound is N-acetylhomocysteine.
5. The method of claim 1 wherein the compound is N,N'-diacetylcystine.
6. The method of claim 1 wherein the compound is N-acetylcysteine.

* * * * *